US00PP16112P3

(12) United States Plant Patent
Oud

(10) Patent No.: US PP16,112 P3
(45) Date of Patent: Nov. 15, 2005

(54) *LOBELIA* PLANT NAMED 'LOBETIS'

(50) Latin Name: *Lobelia×hybrida*
Varietal Denomination: Lobetis

(75) Inventor: Johannes Simon Nicolaas Oud, Bovenkarspel (NL)

(73) Assignee: Syngenta Seeds B.V., Enkhuizen (NL)

( * ) Notice: Subject to any disclaimer, the term of this patent is extended or adjusted under 35 U.S.C. 154(b) by 525 days.

(21) Appl. No.: 10/342,813

(22) Filed: Jan. 15, 2003

(65) Prior Publication Data

US 2004/0139518 P1 Jul. 15, 2004

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—Bruce Vrana; Edouard G. Lebel

(57) ABSTRACT

A new *Lobelia* plant particularly distinguished by its upright compact round plant habit, large flower size and blue and white eye flower color.

1 Drawing Sheet

Latin name of the genus and species of the plant claimed: *Lobelia×hybrida.*
Varietal denomination: 'Lobetis'.

BACKGROUND OF THE NEW PLANT

The present invention comprises a new and distinct cultivar of *Lobelia* plant, botantially known as *Lobelia erinus*. Interspecific *Lobelia* plant resulted from a cross between *Lobelia erinus* and *Lobelia valida.*

The new cultivar is propagated by cuttings resulting from the cross of *Lobelia erinus* 'P140' and *Lobelia valida* 'Y694.' 'P140' (unpatented) is a blue and white eye flower color selection of our own breeding, having a strong growth and a compact spreading plant habit. 'Y694' (unpatented) is a blue and white eye flower color cultivar in *Lobelia valida.*

As a result of this cross, the present cultivar was created in 1999 in Enkhuizen, Netherlands and has been repeatedly asexually reproduced by cuttings in Enkhuizen, Netherlands over a three-year period. It has been found to retain its distinctive characteristics through successive propagations, and this novelty appears to be firmly fixed.

DESCRIPTION OF THE DRAWING

This new *Lobelia* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Lobelia* plant. The data which defines these characteristics were collected from asexual reproductions carried out in Enkhuizen, Netherlands. The plant history was taken on 12 weeks old plants. Color references are primarily to The R.H.S. Colour Chart of The Royal Horticultural Society of London.

Comparison between the new cultivar 'Lobetis' and a similar cultivar

| | 'Lobetis' | 'Blue Star' (unpatented) |
|---|---|---|
| Plant height | 20 cm | 10 cm |
| Plant width | 25 cm | 35 cm |
| Plant shape | Upright | Spreading |
| Flower color | | |
| Upper surface | 99B | 95B |
| Lower surface | 97A | 100A |
| Flower tube | 99C | 95C |

The plant:
*Classification.*—Botanical *Lobelia×hybrida* cv. 'Lobetis'.

Parentage:
*Female parent.*—A seedling named 'P140' is one of our seedings from our P-generation of plants bred in 1989. The plant shape of the female parent is spreading.
*Male parent.*—Asexual propagated 'Y694' is a commercial not patented variety. The plant shape of the male parent is upright, erect.

Plant description:
*Growth habit.*—Upright.
*Plant height.*—20 cm.
*Spreading area of plant.*—25 cm.
*Growth rate.*—Moderate growth.
*Strength.*—Good.
*Branching character.*—Freely branching and lateral branching at every node. Pinching will enhance branching. Branches strong and flexible.
*Blooming period.*—From May until October.

The stem:
*Diameter.*—1.5 mm.
*Texture.*—Smooth, slightly pubescent, glossy.
*Color.*—RHS 138B.
*Length of internode.*—13 mm, depending on the light conditions where the plant is propagated.
*Shape.*—(Tri)angular.

The foliage:

*Shape.*—Leaves simple, generally symmetrical and flat. Broadly ovate with rounded apex, obtuse to attenuate base and crenate margin.

*Texture.*—Slightly pubescent, glossy.

*Length.*—Young 30 mm, fully expanded 55 mm.

*Width.*—Young 10 mm, fully expanded 23 mm.

*Color.*—Upper side: RHS 147A. Lower side: RHS 137B.

The flower:

*Type and habit.*—Flowers form at apical axils, usually one flower per axil. Flowers labiate, upper lip consisting of two small petals and lower lip consisting of three larger and broader petals. Petals are fused at base into a tube. Freely and continuously flowering. Flowers face outward. Flowers persistent. Texture, slightly pubescent. Oblong shape with acute apex and entire margin.

*Flower.*—Width: Upper petals 3 mm, lower petals 8 mm. Length: Upper petals 6 mm, lower petals 12 mm. Depth: 8 mm.

*Texture.*—Smooth, pubescent.

*Buds.*—Length: 8 mm. Diameter: 3 mm. Form: Tubular. Color: Light green.

*Flower color.*—Upper surface: RHS 99B. Lower surface: RHS 97A. Flower tube: RHS 99C.

*Sepals.*—No. of sepals: 5. Length: 7 mm. Width: 1 mm. Texture: Smooth, slightly pubescent. Color: RHS 147A.

*Flower stem.*—Length: 30 mm. Angle: Upright. Strength: Rigid, flexible. Color: RHS 138B.

*Flower throat.*—Color: Upper RHS 100C. Lower white background, blue spots RHS 99B. Texture: Whiskered.

Reproductive organs:

*Androecium.*—Stamen number: 5. Anther shape: Oblong. Anther length: 2 mm. Pollen color: RHS 202B. Amount of pollen: Moderate.

*Gynoecium.*—Pistil length: 9 mm. Stigma shape: Bilobate. Stigma diameter: 1 mm. Stigma color: N87A. Style color: Light green. Ovary color: RHS 138B.

The fruit:

*Fruit size.*—Diameter 2 mm.

*Fruit length.*—4 mm.

*Fruit color.*—RHS 138B.

Seed development: Some seed development has been observed on plants of the new *Lobelia.*

*Seed colour.*—Brown.

*Seed shape.*—Round.

Disease resistance: No susceptibility nor resistance to fungal, bacterial or viral pathogens has been noted.

What is claimed is:

1. A new and distinct variety of *Lobelia* plant, substantially as illustrated and described herein.

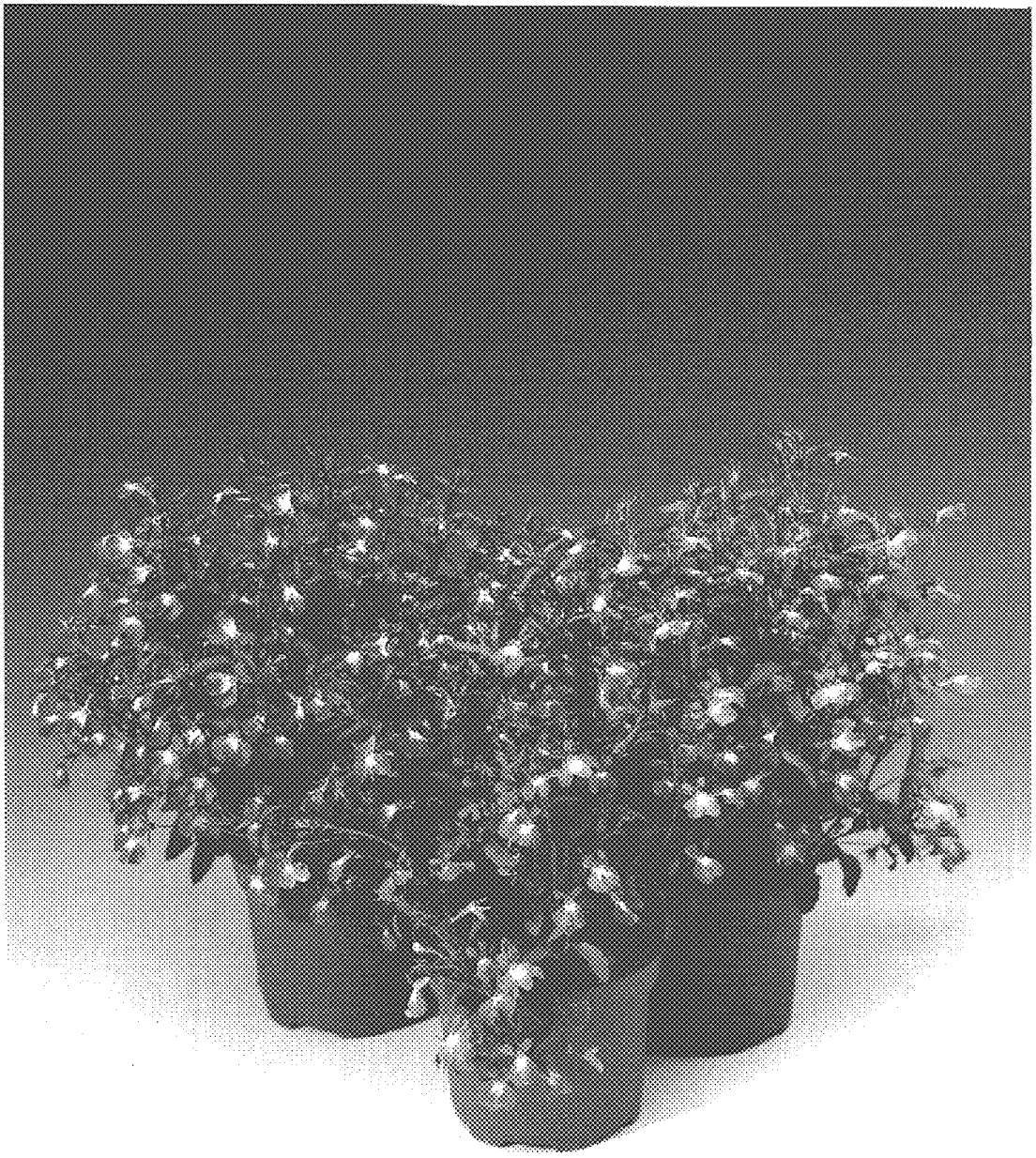

* * * * *